United States Patent [19]

Rose et al.

[11] Patent Number: 4,900,327
[45] Date of Patent: Feb. 13, 1990

[54] PREPARATIONS CONTAINING SUBSTANTIVE NITRODIPHENYLAMINE DERIVATIVE HAIR DYES

[75] Inventors: David Rose, Hilden; Edgar Lieske, Duesseldorf; Norbert Maak, Neuss, all of Fed. Rep. of Germany

[73] Assignee: Henkel Kommanditgesellschaft auf Aktien, Duesseldorf, Fed. Rep. of Germany

[21] Appl. No.: 160,723

[22] Filed: Feb. 26, 1988

[30] Foreign Application Priority Data

Feb. 26, 1987 [DE] Fed. Rep. of Germany ....... 3706223

[51] Int. Cl.⁴ .................... A61K 7/13; C07C 87/54; C07C 143/56
[52] U.S. Cl. ............................................ 8/429; 8/405; 8/407; 8/423; 562/61
[58] Field of Search ................... 8/429, 423, 407, 405; 564/433, 434; 260/508, 509, 510

[56] References Cited

U.S. PATENT DOCUMENTS

| | | | |
|---|---|---|---|
| 3,950,127 | 4/1976 | Halasz et al. | 564/434 |
| 4,254,054 | 3/1981 | Arndt et al. | 260/510 |
| 4,599,450 | 7/1986 | Hertel | 564/433 |
| 4,619,666 | 10/1986 | Rose et al. | 260/509 |
| 4,698,066 | 10/1987 | Rose et al. | 260/508 |
| 4,756,715 | 7/1988 | Rose et al. | 8/429 |

FOREIGN PATENT DOCUMENTS 0469436 11/1950 Canada ................. 260/508

OTHER PUBLICATIONS

Chem Abs. No. 104: 208834y (1985).
Chem Abs. No. 103: 38704v (1985).
Chem Abs. No. 99: 55059a (1982).
Chem Abs. No. 95: 8797x (1981).
Chem Abs. No. 94: 32161k (1981).
Chem Abs. No. 94: 32169u (1981).
Chem Abs. No. 93: 132242k (1980).
Chem Abs. No. 93: 151656q (1980).
Chem Abs. No. 90: 105645a (1978).
Chem Abs. No. 86: 157045s (1976).
Chem Abs. No. 83: 133371g (1975).
Corbett, J., "Hair Dyes" from *The Chemistry of Synthetic Dyes* vol. V (ed. K. Venkatoraman), Academic Press, N.Y. 1971, pp. 508–512.
Chemical Abstracts, vol. 97, No. 4, Jul. 26, 1982, Item 25157x.

Primary Examiner—Paul Lieberman
Assistant Examiner—Linda Skaling
Attorney, Agent, or Firm—Ernest G. Szoke; Wayne C. Jaeschke; Norvell E. Wisdom, Jr.

[57] ABSTRACT

This invention encompasses preparations containing hair dyes of the formula

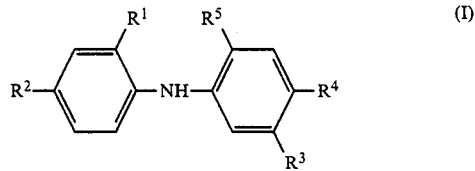

wherein:
one of $R^1$ or $R^2$ is a nitro and the other is $-SO_3H$;
one of $R^3$ or $R^4$ is $-NR^6R^7$ and the other is hydrogen, chlorine, or a $C_{1-4}$ alkyl, and $R^6$ and $R^7$ are independently hydrogen, $C_{1-4}$ alkyl, or $C_{2-4}$ hydroxyalkyl; and
$R^5$ is hydrogen, chlorine, or a $C_{1-4}$ alkyl;
or a water soluble salt thereof; certain novel compounds within the above formula; and a method for dyeing hair.

22 Claims, No Drawings

PREPARATIONS CONTAINING SUBSTANTIVE NITRODIPHENYLAMINE DERIVATIVE HAIR DYES

BACKGROUND OF THE INVENTION

1. Field of the Invention

This invention relates to hair dye preparations containing substantive hair dyes as well as some of the dyes per se. Preparations of the type in question contain substantive hair dyes in a cosmetic carrier. In many cases, such preparations additionally contain oxidation dye precursors to produce certain shades. The cosmetic carriers used for the substantive hair dyes and oxidation dye precursors, if any, are creams, emulsions, gels, shampoos, foam aerosols or other preparations suitable for application to the hair.

2. Statement of Related Art

In addition to the oxidation dyes, which are formed by the oxidative coupling of one or more developer components with one or more coupler components, substantive hair dyes play a prominent part in the dyeing of hair. Substantive dyes have the advantage of being used without the addition of oxidizing agents. The substantive dyes used are predominantly nitrobenzene derivatives. They are used either on their own or in combination with other substantive dyes, cationic azo dyes such as anthraquinone dyes, indophenols, triphenylmethane dyes, or with oxidation dyes.

Good hair-dyeing preparations have to form the required shades with sufficient intensity. They must be readily absorbed by human hair without excessively staining the scalp. The coloring produced with them must show high stability to light, heat, perspiration, shampoos and the chemicals used in the permanent waving of hair. Finally, they should be safe to use from the toxicological and dermatological viewpoint.

Among the substantive nitrobenzene derivatives, the nitroanilines and derivatives thereof play an important part because some of these dyes produce intensive, light-stable colors. However, the known substantive nitroaniline dyes have disadvantages in that, on the one hand, they show only limited solubility in water, which leads to problems during formulation of the hair dye preparations, and on the other hand they are not sufficiently fast to washing, i.e. the dye finishes fade considerably after repeated shampooing.

In addition, it is desirable that substantive dyes should be able to produce shades of red to obtain fashionable hair colors. 2-Nitro-p-phenylenediamine and amino-substituted derivatives thereof are normally used for this purpose. Unfortunately, these chemically related compounds are difficult to dissolve and difficult to disperse in water. This readily leads to uneven or to faint hair colors. Moreover, particularly where hair preparations have high concentrations of dye, the dyes crystallize out and are not adsorbed onto the hair to be dyed. Accordingly, there is an urgent need for substantive hair dyes showing improved solubility in water.

Furthermore, substantive hair dyes desireably show high compatibility with other dyes, for example with oxidation dye precursors and with the other components normally used in oxidation hair dye preparations, because substantive dyes and oxidation dyes are often combined with one another for color modification. Accordingly, high stability to reducing agents and oxidizing agents is necessary.

DESCRIPTION OF THE INVENTION

Other than in the operating examples, or where otherwise indicated, all numbers expressing quantities of ingredients or reaction conditions used herein are to be understood as modified in all instances by the term "about".

This invention provides hair dye preparations containing one or more substantive hair dyes, in an aqueous cosmetic carrier, in which the substantive hair dyes are one or more compounds of the formula:

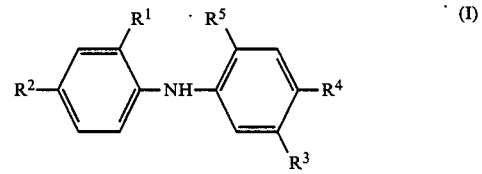

wherein: one of $R^1$ or $R^2$ is a nitro and the other an $-SO_3H$; and either $R^3$ or $R^4$ is $-NR^6R^7$, where $R^6$ and $R^7$ are independently hydrogen, $C_{1-4}$ alkyl or $C_{2-4}$ hydroalkyl, while the other of $R^3$ or $R^4$ is hydrogen, chlorine, or a $C_{1-4}$ alkyl; and $R^5$ is hydrogen, chlorine or a $C_{1-4}$ alkyl; as well as the water soluble salts of the above compounds.

Among the compounds corresponding to formula (I), those in which $R^3$ is hydrogen, $R^4$ is $-NR^6R^7$ and $R^5$ is hydrogen, chlorine or a methyl group are particularly preferred.

The nitrodiphenylamine derivatives corresponding to formula (I) produce deep yellow to red-brown colors of high intensity, light stability and fastness to shampooing of the hair.

The compounds corresponding to formula (I), wherein: one of $R^1$ or $R^2$ is nitro and the other is $-SO_3H$; $R^3$ is hydrogen; $R^4$ is of the formula $-NR^6R^7$, where $R^6$ independently are hydrogen, $C_{1-4}$ alkyl or $C_{2-4}$ hydroxyalkyl; $R^5$ is hydrogen, chlorine or $C_{1-4}$ alkyl; as well as water soluble salts of the above compounds, are novel and, accordingly, are per se a subject of the present invention.

The novel inventive nitrodiphenylamine derivative are generally prepared by reaction of 4-chloro-3-nitrobenzenesulfonic acid alkali salt or of 2-chloro-5-nitrobenzenesulfonic acid alkali salt with a paraphenylenediamine corresponding to the formula

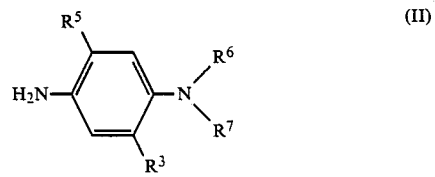

wherein $R^3$, $R^5$, $R^6$ and $R^7$ are as defined for formula (I), with the elimination of HCl in the presence of a base, for example an alkali carbonate.

In the context of the invention, water soluble salts are primarily understood to be the salts of strong bases, including: alkali salts, such as sodium or potassium, ammonium salts, $C_{2-4}$ alkanolammonium salts such as monoethanolammonium, triethanolammonium, or isopropanolammonium, sodium being preferred.

The hair dye preparations according to the invention may contain the (first) substantive nitrodiphenylamine derivatives corresponding to formula (I) either alone or in combination with known other (second) substantive dyes, for example with other nitrobenzene derivatives, anthraquinone dyes, triphenylmethane dyes or azo dyes. When present the second substantive hair dyes are in any amount effective to alter the color of hair to be treated to a desired degree. In a further invention embodiment, the substantive dyes of general formula (I), by virtue of their high resistance to reducing agents and oxidizing agents, are also eminently suitable for combination with oxdation dye precursors, i.e. for modifying the shades of oxidation hair dye preparations. Oxidation hair dye preparations contain as dye precursors developer components which form the oxidation dyes by oxidative coupling with one other or with suitable coupler components. Suitable developer components useful in this invention include primary aromatic amines containing another free or substituted hydroxy or amino moiety in the para or ortho position, diaminopyridine derivatives, heterocyclic hydrazones, 4-aminopyrazolone derivatives and 2,4,5,6-tetraaminopyrimidine and derivatives thereof. Suitable coupler components useful in this invention include m-phenylenediamine derivatives, naphthols, resorcinol and resorcinol derivatives, pyrazolones and m-aminophenols. The couplers and developers, when present, are in oxidative hair dye effective amounts in relation to each other. The combined oxidative hair dye precursors, with the required oxidizing agent present in an oxidizing agent effective amount, may be present in any amount effective to alter the color of hair to be treated, to a desired degree.

To produce the hair dye preparations according to the invention, the first and optional second substantive hair dyes and the optional oxidation dye precursors, if any, are incorporated in suitable cosmetic carriers, such as creams, emulsions, gels, surfactant-containing foaming solutions such as shampoos, foam aerosols, or other preparations which are suitable for application to the hair.

Standard constituents of cosmetic preparations such as the above include: wetting agents and emulsifiers such as anionic, nonionic or ampholytic surfactants, preferably fatty alcohol sulfates, alkanesulfonates, alpha-olefin sulfonates, fatty alcohol polyglycol ether sulfates, ethylene oxide adducts with fatty alcohols, fatty acid adducts with alkylphenols, sorbitan fatty acid esters and fatty acid partial glycerides, and fatty acid alkanolamides; thickeners such as methyl or hydroxyethyl cellulose, starch, fatty alcohols, paraffin oils, and fatty acids; and perfume oils and hair-care additives such as water soluble cationic polymers, protein derivatives, pantotheic acid and cholesterol. The constituents of the cosmetic carriers are used in the usual quantities effective for preparing the hair dye preparations according to the invention. For example, emulsifiers are used in concentrations of 0.5 to 30% by weight and thickeners in concentrations of 0.1 to 25% by weight.

In the hair dye preparations according to the invention, the substantive hair dyes corresponding to general formula (I) preferably are used in a quantity of from 0.01 to 5.0% by weight, most preferably 0.1 to 2% by weight. In addition, known oxidation hair dye precursors (developer and coupler components, etc.) preferably are present in a combined quantity of from 0.01 to 5.0% by weight, most preferably 1.0 to 3.0% by weight.

If the hair dye preparation according to the inventin contains oxidation dye precursors, it also is advisable to add a small quantity of a reducing agent, for example from 0.5 to 2.0% by weight of sodium sulfite, to stabilize the oxidation dye precursors. In this case, an oxidizing agent is added to the hair dye preparation before use in order to initiate oxidative development of the oxidation dye precursors. Oxidizing agents useful in this invention include, in particular, hydrogen peroxide or adducts thereof with urea, melamine or sodium borate as well as mixtures of these hydrogen peroxide adducts with potassium peroxysulfate. All of the above weights are based upon the weight of the hair dye preparation as a whole, it being understood that water is employed q.s. to 100%.

The hair dye preparations according to the invention may be used in a mildly acidic, neutral or alkaline medium, irrespective of the cosmetic carrier used, for example a cream, gel or shampoo. The hair dye preparations preferably have a pH range from 8 to 10. They may be used at temperatures of from 15° to 40° C. After a contact time of around 30 minutes, the hair dye preparation is removed by rinsing from the hair to be dyed. The hair may then be washed with a mild shampoo and dried. Washing with a shampoo is unnecessary when a carrier of high surfactant content, for example a dye shampoo, is used.

Hair dye finishes of high intensity, good fastness properties particularly to shampooing, and high stability to bleeding and changes in color during shampooing may be obtained with the hair dye preparations according to the invention. The following Examples are intended to illustrate the invention without limiting it in any way.

EXAMPLES

Production Examples 1. 2-Nitro-4'-N,N-bis(2-hydroxyethyl)-aminodiphenylamine-4-sulfonic acid, sodium salt A mixture of (A) 6.5 g (0.025 mol) 4-chloro-3-nitrobenzenesulfonic acid, Na salt and (B) 4.9 g (0.025 mol) N,N-bis-(2-hydroxyethyl)-p-phenylenediamine, 2.54 g (0.027 mol) sodium carbonate and 10 ml water were heated for 7 hours to 120° C. in autoclave. After cooling, the solution was concentrated to dryness. The residue was recrystallized from a mixtue of ethanol and water. Yield: red-brown crystals, TLC (silica gel 60F-254/Merck) eluent: n-butanol/acetic acid/water=8:2:1; RF=0.42.

2. 2-Nitro-2'-methyl-4'-aminodiphenylamine-4-sulfonic acid, sodium salt

Preparation was carried out in the same way as in Example 1 starting from
(A) 4-chloro-3-nitrobenzenesulfonic acid, Na salt and
(B) p-tolylenediamine.
Yield: rust red powder, TLC (silica gel 60F-254/Merck) eluent: n-butanol/acetic acid/H$_2$O=8:2:1; RF=0.43.

3. 2-Nitro-2'-chloro-4'-aminodiphenyllamine-4-sulfonic acid, sodium salt

Preparation was carried out as described in Example 1 starting from
(A) 4-chloro-3-nitrobenzensulfonic acid, Na salt and
(B) 2-chloro-1,4-phenylenediamine.
Yield: red powder, melting point above 250° C.

4. 2-Nitro-4'-dimethylaminodiphenylamine-4-sulfonic acid, sodium salt

Preparation was carried out as described in Example 1 starting from
(A) 4-chloro-3-nitrobenzenesulfonic acid, Na salt and (B) N,N-dimethyl-p-phenylenediamine.

Yield: dark brown crystals, melting point above 250° C.

5. 4-Nitro-4'-N,N-bis(2-hydroxyethyl)-aminodiphenylamine-2-sulfonic acid, sodium salt Preparation was carried out as described in Example 1 starting from
(A) 2-chloro-5-nitrobenzenesulfonic acid, Na salt and
(B) N,N-bis-(2-hydroxyethyl)-p-phenylenediamine.

Yield: red powder, TLC (silica gel 60F-254/Merck) eluent: n-butanol/acetic acid/water=8:2:1; RF=0.47.

6. 4-Nitro-4'-dimethylaminodiphenylamine-2-sulfonic acid, sodium salt

Preparation was carried out as described in Example 1 starting from
(A) 2-chloro-5-nitrobenzenesulfonic acid, Na salt and
(B) N,N-dimethyl-p-phenylenediamine.

Yield: red-brown crystals, melting point approx. 250° C.

7. 4-Nitro-3'-dimethylaminodiphenylamine-2-sulfonic acid

Preparation was carried out in accordance with Journ. Chem. Soc. (1948), 1229.

Yield: yellow-brown crystals, melting point approx. 240° C. (with decomposition).

Hair dye tests

Hair dye creams were prepared from the following constituents:

| | |
|---|---|
| $C_{12-18}$ fatty alcohol | 10 g |
| $C_{12-14}$ fatty alcohol + 2 EO sulfate, Na salt (28%) | 25 g |
| Water | 60 g |
| Substantive dye according to formula I | 1 g |
| Ammonium sulfate | 1 g |
| Concentrated ammonia solution to pH | 9.5 g |
| Water q.s. ad | 100 g |

The constituents were mixed together in the above order. After addition of the substantive dyes, the pH of the emulsion was first adjusted to 9.5 with concentrated ammonia solution, after which the emulsion was made up with water to 100 g.

The dye cream was applied to approx. 5 cm long strands of standardized, 90% grey, but not specially pretreated human hair and left thereon for 30 minutes at 27° C. After dyeing, the hair was rinsed, washed with a standard shampoo and then dried.

The compounds of Examples 1 to 7 were used as substantive hair dyes.

The results of the dyeing tests are shown in the Table below.

TABLE

Results of hair dye tests

| Substantive dye of Example no. | Color of the dyed hair |
|---|---|
| 1 | brown |
| 2 | red-blond |
| 3 | grey-orange |
| 4 | brown |
| 5 | yellow-brown |
| 6 | yellow |
| 7 | deep yellow |

The above table indicates that hair colors obtained using the substantive dyes according to the invention are particularly desireable. When this is combined with the inventive dyes' excellent water dispersibility or solubility, the result is a very valuable product.

We claim:

1. In a hair dye aqueous preparation comprising a hair dye effective amount of a first substantive hair dye in a suitable cosmetic carrier, the improvement wherein said first substantive hair dye comprises at least one of the formula:

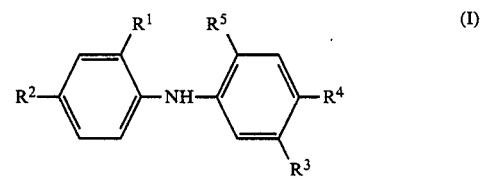

wherein:
one of $R^1$ or $R^2$ is nitro and the other is $-SO_3H$;
one of $R^4$ or $R^4$ is $-NR^6R^7$ and the other is hydrogen, chlorine, or a $C_{1-4}$ alkyl, and $R^6$ and $R^7$ are independently hydrogen, $C_{1-4}$ alkyl, or $C_{2-4}$ hydroxyalkyl; and
$R^5$ is hydrogen, chlorine, or a $C_{1-4}$ alkyl;
or a water soluble salt thereof.

2. The hair dye preparation of claim 1 wherein in the formula:
$R^3$ is hydrogen;
$R^4$ is $NR^6R^7$; and
$R^5$ is hydrogen, chlorine, or methyl.

3. The hair dye preparation of claim 1 wherein said first substantive hair dye is a water soluble salt of sodium, potassium, ammonium, or a $C_{2-4}$ alkanolammonium.

4. The hair dye preparation of claim 2 wherein said first substantive hair dye is a water soluble salt of sodium, potassium, ammonium, or a $C_{2-4}$ alkanolammonium.

5. The hair dye preparation of claim 1 wherein said first substantive hair dye is 2-nitro-4'-N,N-bis-(2-hydroxyethyl)-aminodiphenylamine-4-sulfonic acid, sodium salt.

6. The hair dye preparation of claim 1 wherein said first substantive hair dye is 2-nitro-2'-methyl-4'-aminodiphenylamine-4-sulfonic acid, sodium salt.

7. The hair dye preparation of claim 1 wherein said first substantive hair dye is 2-nitro-2'-chloro-4'-aminodiphenylamine-4-sulfonic acid, sodium salt.

8. The hair dye preparation of claim 1 wherein said first substantive hair dye is 2-nitro-4'-dimethylaminodiphenylamine-4-sulfonic acid, sodium salt.

9. The hair dye preparation of claim 1 wherein said first substantive hair dye is 4-nitro-4'-N,N-bis-(2-hydroxyethyl)-aminodiphenylamine-2-sulfonic acid, sodium salt.

10. The hair dye preparation of claim 1 wherein said first substantive hair dye is 4-nitro-4'-dimethylaminodiphenylamine-2-sulfonic acid, sodium salt.

11. The hair dye preparation of claim 1 wherein said first substantive hair dye is 4-nitro-3'-dimethylaminodiphenylamine-2-sulfonic acid.

12. The hair dye of preparation of claim 1 in which said first substantive hair dye is present in about 0.01 to 5.0% by weight, based upon the weight of the hair dye preparation as a whole.

13. The hair dye preparation of claim 1 wherein at least one second substantive hair dye, at least one oxidative hair dye precursor, or both, are present in an amount effective to alter the color of hair to be treated to a desired degree.

14. The hair dye preparation of claim 1 wherein at least one oxidative hair dye precursor is present in a combined quantity of about 0.01 to about 5.0% by weight, based on the weight of the hair dye preparation as a whole.

15. The hair dye preparation of claim 1, formulated as a cream, an emulsion, a gel, a shampoo, or an aerosol foam.

16. The hair dye preparation of claim 13 or 14, formulated as a cream, an emulsion, a gel, a shampoo, or an aerosol foam.

17. A method for dyeing hair comprising
applying to the hair a hair-dyeing effective amount of the preparation of claim 1;
permitting said preparation to remain on said hair for a hair-dyeing effective time; and
removing said hair dye from said hair.

18. A compound selected from the group consisting of 2-nitro-4'-N,N-bis-(2-hydroxyethyl)-aminodiphenylamine-4-sulfonic acid, the water soluble salts thereof, 2-nitro-2'-methyl-4'-aminodiphenylamine-4-sulfonic acid, the water soluble salts thereof, 2-nitro-2'-chloro-4'-aminodiphenylamine-4-sulfonic acid, the water soluble salts thereof, 2-nitro-2'-chloro-4'-dimethylaminodiphenylamine-4-sulfonic acid, the water soluble salts thereof, 4-nitro-4'-N,N-bis-(2-hydroxyethyl)-aminodiphenylamine-4-sulfonic acid, and the water soluble salts thereof.

19. The compound of claim 18 having the formula: 2-nitro-4'-N,N-bis-(2-hydroxyethyl)-aminodiphenylamine-4-sulfonic acid, sodium salt.

20. The compound of claim 18 having the formula: 2-nitro-4'-dimethylaminodiphenylamine-4-sulfonic acid, sodium salt.

21. The compound of claim 18 having the formula: 4-nitro-4'-N,N-bis-(2-hydroxyethyl)-aminodiphenylamine-2-sulfonic acid, sodium salt.

22. The compound of claim 18 having the formula: 4-nitro-4'-dimethylaminodiphenylamine-2-sulfonic acid, sodium salt.

* * * * *

UNITED STATES PATENT AND TRADEMARK OFFICE
CERTIFICATE OF CORRECTION

PATENT NO. : 4,900,327
DATED : February 13, 1990
INVENTOR(S) : David Rose et al.

It is certified that error appears in the above-identified patent and that said Letters Patent is hereby corrected as shown below:

In Claim 1, Col. 6, line 20, "$R^4$ or $R^4$ is" should read --$R^3$ or $R^4$ is--.

Signed and Sealed this

Second Day of April, 1991

Attest:

HARRY F. MANBECK, JR.

*Attesting Officer*  *Commissioner of Patents and Trademarks*